(12) United States Patent
Kim et al.

(10) Patent No.: US 9,284,550 B2
(45) Date of Patent: Mar. 15, 2016

(54) **SINGLE-STRANDED NUCLEIC ACID APTAMERS SPECIFICALLY BINDING TO *KLEBSIELLA PNEUMONIAE* AND METHOD FOR DETECTING *K. PNEUMONIA* USING THE SAME**

(71) Applicant: KOREA INSTITUTE OF SCIENCE AND TECHNOLOGY, Seoul (KR)

(72) Inventors: Byoung Chan Kim, Seoul (KR); Yeon Seok Kim, Goyang-si (KR); Jin Yang Chung, Seoul (KR); Jong Soo Jurng, Seoul (KR); Min Young Song, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

(21) Appl. No.: 14/446,651

(22) Filed: Jul. 30, 2014

(65) Prior Publication Data

US 2015/0141270 A1 May 21, 2015

(30) Foreign Application Priority Data

Nov. 20, 2013 (KR) .................. 10-2013-0141753

(51) Int. Cl.
| | | |
|---|---|---|
| *C07H 21/02* | (2006.01) |
| *C07H 21/04* | (2006.01) |
| *C12Q 1/68* | (2006.01) |
| *G01N 33/50* | (2006.01) |
| *C12N 15/11* | (2006.01) |
| *G01N 33/53* | (2006.01) |
| *G01N 33/569* | (2006.01) |
| *C12N 15/115* | (2010.01) |

(52) U.S. Cl.
CPC .............. *C12N 15/11* (2013.01); *C12N 15/115* (2013.01); *G01N 33/5308* (2013.01); *G01N 33/56916* (2013.01); *C12N 2310/16* (2013.01); *C12N 2310/3181* (2013.01); *C12N 2320/11* (2013.01); *G01N 2333/26* (2013.01)

(58) Field of Classification Search
None
See application file for complete search history.

(56) References Cited

U.S. PATENT DOCUMENTS

2007/0292397 A1* 12/2007 McNulty et al. ............. 424/93.6
2011/0236410 A1*  9/2011 Bakshi et al. ............. 424/190.1

OTHER PUBLICATIONS

Kim, Yeon Seok, et al. "Isolation and characterization of DNA aptamers against *Escherichia coli* using a bacterial cell—systematic evolution of ligands by exponential enrichment approach." Analytical biochemistry 436.1 (2013): 22-28.

* cited by examiner

*Primary Examiner* — Richard Schnizer
(74) *Attorney, Agent, or Firm* — NSIP Law

(57) ABSTRACT

Provided is a single-stranded nucleic acid aptamer specifically binding to *Klebsiella pneumoniae*, and a method for detecting *Klebsiella pneumoniae* by using the same. The aptamer of the present disclosure, and a method, a composition, a kit or a sensor of using the same may be used to specifically detect *Klebsiella pneumoniae* present in an aqueous environment, foods, and medical samples and also be applied in fields such as sanitary conditions of foods and medical diagnosis.

10 Claims, 5 Drawing Sheets

SEQUENCE LISTING

```
<160> NUMBER OF SEQ ID NOS: 28

<210> SEQ ID NO 1
<211> LENGTH: 45
<212> TYPE: DNA
<213> ORGANISM: Artificial Sequence
<220> FEATURE:
<223> OTHER INFORMATION: ssDNA K1

<400> SEQUENCE: 1
gagtcggtgg tgttcccaga tggaagccgc agtaatagtg cagct            45

<210> SEQ ID NO 2
<211> LENGTH: 45
<212> TYPE: DNA
<213> ORGANISM: Artificial Sequence
<220> FEATURE:
<223> OTHER INFORMATION: ssDNA K2

<400> SEQUENCE: 2
aatcaggctc agcatggagt tgcgaggcca atatccggtt aagcg            45

<210> SEQ ID NO 3
<211> LENGTH: 45
<212> TYPE: DNA
<213> ORGANISM: Artificial Sequence
<220> FEATURE:
<223> OTHER INFORMATION: ssDNA K3

<400> SEQUENCE: 3
```

```
tgtccttcag acccctgatt tgattaatat tcttaaagtc ttcag          45
```

```
<210> SEQ ID NO 4
<211> LENGTH: 45
<212> TYPE: DNA
<213> ORGANISM: Artificial Sequence
<220> FEATURE:
<223> OTHER INFORMATION: ssDNA K4

<400> SEQUENCE: 4
ctttataaca ctgttactat cgcctgttag aggtaatgag ttctt          45
```

```
<210> SEQ ID NO 5
<211> LENGTH: 45
<212> TYPE: DNA
<213> ORGANISM: Artificial Sequence
<220> FEATURE:
<223> OTHER INFORMATION: ssDNA K5

<400> SEQUENCE: 5
ataccgcatg gatgaggtgt tgtacttggg tgctgggggg gtctg          45
```

```
<210> SEQ ID NO 6
<211> LENGTH: 45
<212> TYPE: DNA
<213> ORGANISM: Artificial Sequence
<220> FEATURE:
<223> OTHER INFORMATION: ssDNA K6

<400> SEQUENCE: 6
ttttacagct aaaccggtgt aatgtccttg ttcttcatac ataca          45
```

```
<210> SEQ ID NO 7
<211> LENGTH: 45
<212> TYPE: DNA
<213> ORGANISM: Artificial Sequence
<220> FEATURE:
<223> OTHER INFORMATION: ssDNA K8

<400> SEQUENCE: 7
tcttttaggg agtccctatt aagtattgta accttaggac tgaat          45
```

```
<210> SEQ ID NO 8
<211> LENGTH: 45
<212> TYPE: DNA
<213> ORGANISM: Artificial Sequence
<220> FEATURE:
<223> OTHER INFORMATION: ssDNA K9

<400> SEQUENCE: 8
cttaactagt tgcatgggtc ctgctcgagg gatcgtgggt gatgg          45
```

```
<210> SEQ ID NO 9
<211> LENGTH: 45
<212> TYPE: DNA
<213> ORGANISM: Artificial Sequence
<220> FEATURE:
<223> OTHER INFORMATION: ssDNA K10

<400> SEQUENCE: 9
atgactcatt ggtgcttcgc attttactgc atctcctaat attgg          45
```

```
<210> SEQ ID NO 10
<211> LENGTH: 45
<212> TYPE: DNA
```

-continued

```
<213> ORGANISM: Artificial Sequence
<220> FEATURE:
<223> OTHER INFORMATION: ssDNA K11

<400> SEQUENCE: 10
tcttttaggg agtccctatt aagtattgta accttaggac tgaat            45

<210> SEQ ID NO 11
<211> LENGTH: 45
<212> TYPE: DNA
<213> ORGANISM: Artificial Sequence
<220> FEATURE:
<223> OTHER INFORMATION: ssDNA K13

<400> SEQUENCE: 11
gggtgcgcgg gttaatagat tttataaaaa gttgtgcctg tcgtt            45

<210> SEQ ID NO 12
<211> LENGTH: 45
<212> TYPE: DNA
<213> ORGANISM: Artificial Sequence
<220> FEATURE:
<223> OTHER INFORMATION: ssDNA K14

<400> SEQUENCE: 12
cggcagttgg tttttctgt tctgcatagg atgctcttag tcggc             45

<210> SEQ ID NO 13
<211> LENGTH: 45
<212> TYPE: DNA
<213> ORGANISM: Artificial Sequence
<220> FEATURE:
<223> OTHER INFORMATION: ssDNA K17

<400> SEQUENCE: 13
agtcttatgg agcggtcgac aacgtcaccg ccctgtggt gaggt             45

<210> SEQ ID NO 14
<211> LENGTH: 45
<212> TYPE: DNA
<213> ORGANISM: Artificial Sequence
<220> FEATURE:
<223> OTHER INFORMATION: ssDNA K18

<400> SEQUENCE: 14
atggcaccct tgcaagcgaa cctgggtttt tagtcgttag cattg            45

<210> SEQ ID NO 15
<211> LENGTH: 44
<212> TYPE: DNA
<213> ORGANISM: Artificial Sequence
<220> FEATURE:
<223> OTHER INFORMATION: ssDNA K19

<400> SEQUENCE: 15
tcatagagtg taactaacta gtcgttgatg cggttggctt tagc             44

<210> SEQ ID NO 16
<211> LENGTH: 45
<212> TYPE: DNA
<213> ORGANISM: Artificial Sequence
<220> FEATURE:
<223> OTHER INFORMATION: ssDNA K20

<400> SEQUENCE: 16
gatattgact aagaggtggt tgtctccttt tgctaaatct cgctc            45
```

<210> SEQ ID NO 17
<211> LENGTH: 45
<212> TYPE: DNA
<213> ORGANISM: Artificial Sequence
<220> FEATURE:
<223> OTHER INFORMATION: ssDNA K21

<400> SEQUENCE: 17
atgcaccagg gatgtatatt gtctggctgt cttctttgga cgcgt            45

<210> SEQ ID NO 18
<211> LENGTH: 45
<212> TYPE: DNA
<213> ORGANISM: Artificial Sequence
<220> FEATURE:
<223> OTHER INFORMATION: ssDNA K22

<400> SEQUENCE: 18
atgtgctgga agcgccacag gattattggt gacgtgtttg cgctt            45

<210> SEQ ID NO 19
<211> LENGTH: 45
<212> TYPE: DNA
<213> ORGANISM: Artificial Sequence
<220> FEATURE:
<223> OTHER INFORMATION: ssDNA K23

<400> SEQUENCE: 19
gttgtgtcta tactcagctt cttgttactt tactggacat ctatc            45

<210> SEQ ID NO 20
<211> LENGTH: 44
<212> TYPE: DNA
<213> ORGANISM: Artificial Sequence
<220> FEATURE:
<223> OTHER INFORMATION: ssDNA K24

<400> SEQUENCE: 20
gggagcttat gtagaagcaa aggtgcgatg ctgggtgagc gtta             44

<210> SEQ ID NO 21
<211> LENGTH: 45
<212> TYPE: DNA
<213> ORGANISM: Artificial Sequence
<220> FEATURE:
<223> OTHER INFORMATION: ssDNA K25

<400> SEQUENCE: 21
ttacgagcgg gcggggttta gtgtttctgt gggttctgtt tcata            45

<210> SEQ ID NO 22
<211> LENGTH: 45
<212> TYPE: DNA
<213> ORGANISM: Artificial Sequence
<220> FEATURE:
<223> OTHER INFORMATION: ssDNA K26

<400> SEQUENCE: 22
gcaactggat tacgtacctt gctttgtgaa cttacttgtc accca            45

<210> SEQ ID NO 23
<211> LENGTH: 45
<212> TYPE: DNA
<213> ORGANISM: Artificial Sequence
<220> FEATURE:

```
<223> OTHER INFORMATION: ssDNA K27

<400> SEQUENCE: 23
cgaccacact tccctggaac tctgagttgg cactctgccg cagct            45

<210> SEQ ID NO 24
<211> LENGTH: 45
<212> TYPE: DNA
<213> ORGANISM: Artificial Sequence
<220> FEATURE:
<223> OTHER INFORMATION: ssDNA K28

<400> SEQUENCE: 24
cggcttcatt tctgtgttgg ttgcgtttgt gtggggattt ctcat            45

<210> SEQ ID NO 25
<211> LENGTH: 45
<212> TYPE: DNA
<213> ORGANISM: Artificial Sequence
<220> FEATURE:
<223> OTHER INFORMATION: ssDNA K29

<400> SEQUENCE: 25
gttgtgtcta tactcagctt cttgttactt tactggacat ctatc            45

<210> SEQ ID NO 26
<211> LENGTH: 88
<212> TYPE: DNA
<213> ORGANISM: Artificial Sequence
<220> FEATURE:
<223> OTHER INFORMATION: ssDNA library
<220> FEATURE:
<221> NAME/KEY: misc_feature
<222> LOCATION: (20)..(64)
<223> OTHER INFORMATION: n is a, c, g, or t

<400> SEQUENCE: 26
gcaatggtac ggtacttccn nnnnnnnnnn nnnnnnnnnn nnnnnnnnnn nnnnnnnnnn    60
nnnncaaaag tgcacgctac tttgctaa                                      88

<210> SEQ ID NO 27
<211> LENGTH: 19
<212> TYPE: DNA
<213> ORGANISM: Artificial Sequence
<220> FEATURE:
<223> OTHER INFORMATION: forward primer

<400> SEQUENCE: 27
gcaatggtac ggtacttcc                                         19

<210> SEQ ID NO 28
<211> LENGTH: 24
<212> TYPE: DNA
<213> ORGANISM: Artificial Sequence
<220> FEATURE:
<223> OTHER INFORMATION: reverse primer

<400> SEQUENCE: 28
ttagcaaagt agcgtgcact tttg                                   24
```

SINGLE-STRANDED NUCLEIC ACID APTAMERS SPECIFICALLY BINDING TO KLEBSIELLA PNEUMONIAE AND METHOD FOR DETECTING K. PNEUMONIA USING THE SAME

RELATED APPLICATIONS

This application claims the benefit of Korean Patent Application No. 10-2013-0141753, filed on Nov. 20, 2013, in the Korean Intellectual Property Office, the disclosure of which is incorporated herein in its entirety by reference.

BACKGROUND

1. Field

One or more embodiments of the present invention relate to a single-stranded nucleic acid aptamer specifically binding to *Klebsiella pneumoniae*, and a method for detecting *Klebsiella pneumoniae* by using the same.

2. Description of the Related Art

*Klebsiella pneumoniae* is known as multiantibiotic-resistant bacteria which causes pneumonia in humans. *Klebsiella pneumoniae*, which belongs to a fecal coliform, is discovered in various environments, and in particular, is allegedly frequently discovered in aqueous environments due to release via feces. Accordingly, periodic measurement and management of *Klebsiella pneumoniae* in aqueous environments is necessary. Authorized test methods for fecal coliforms, such as membrane filtration method and most probable number (MPN) method quantitate the presence of coliforms based on lactose degradation capability. However, the test methods require at least 4 days to obtain results, and the results are unreliable due to a large error because they are calculated based on statistical tables.

At present, there is no method for promptly detecting the presence of *Klebsiella pneumoniae*. The technical difficulty in prompt detection of *Klebsiella pneumoniae* makes it difficult to immediately respond to *Klebsiella pneumoniae* contamination, and thus the analysis of *Klebsiella pneumoniae* contamination is usually restricted to post-management. Accordingly, a sensor system capable of monitoring the presence of *Klebsiella pneumoniae* in various environments including an aqueous condition is required. In particular, for the development of the sensor system, it is essential to develop a receptor which can recognize, with high affinity, the presence of *Klebsiella pneumoniae*.

An aptamer used herein refers to a nucleic acid or a peptide molecule having high specificity and affinity for various target materials such as heavy metal ions, organic compounds, proteins, bacteria, and cancer cells. Aptamers have advantages over antibiotics in that aptamers are more stable and also can more easily obtain target material-specific receptors than antibiotics and thus research on the development of aptamers on target materials has been actively performed. Various chemical functional groups may be provided at ends of an aptamer, and the specificity and affinity of the aptamer for various target materials can be maximized via repeated adsorption/desorption of particular nucleotide sequences which bind to target materials. Additionally, once the nucleotide sequences of aptamers are obtained their chemical synthesis is rather easy, thus enabling a low cost and large scale production of aptamers with high purity. Furthermore, the specificity of aptamers for target materials may be increased by reducing the degree of non-specificity via a counter-selection step which utilizes materials analogous to target materials.

Accordingly, the present disclosure provides single-stranded nucleic acid aptamers specifically binding to *Klebsiella pneumoniae*, and a method of detecting *Klebsiella pneumoniae* by using the same.

SUMMARY

In an aspect of the present invention, there is provided a single-stranded nucleic acid aptamer specifically binding to *Klebsiella pneumoniae*.

In an aspect of the present invention, there is provided a composition, a sensor, and a kit for detecting *Klebsiella pneumoniae* including a single-stranded nucleic acid aptamer which specifically binds to *Klebsiella pneumoniae*.

In a further aspect of the present invention, there is provided a method for detecting *Klebsiella pneumoniae* in a sample by using a single-stranded nucleic acid aptamer which specifically binds to *Klebsiella pneumoniae*.

Additional aspects will be set forth in part in the description which follows and, in part, will be apparent from the description, or may be learned by practice of the presented embodiments.

In an aspect, the present disclosure provides a single-stranded nucleic acid aptamer which specifically binding to *Klebsiella pneumoniae*. The term, "aptamer" used herein, refers to a molecule having a stable three-dimensional structure and is capable of binding to a target molecule with high affinity and specificity. The term, "specifically binding" used herein, refers to binding of the aptamers of the present disclosure only to *Klebsiella pneumoniae* exclusive of other microorganisms. The term, "nucleic acid" used herein, refers to a polymer of nucleotides, and may be used the same meaning as "oligonucleotide" or "polynucleotide". The nucleic acid may include DNA, RNA, and/or peptide nucleic acid (PNA). A nucleotide is a basic constitutional unit of a nucleic acid molecule which includes deoxyribose nucleotide or ribose nucleotide, and may include an analogue where a sugar or a base is modified in addition to natural nucleotides. Accordingly, the term, "single-stranded nucleic acid" used herein, refers to a type of nucleic acid where the nucleotide polymer is single stranded.

The aptamer may bind specifically to the surface of *Klebsiella pneumoniae*. The term, "the surface of *Klebsiella pneumoniae*" used herein, refers to proteins, lipids, or other particular structures present on the surface of *Klebsiella pneumoniae* cells. The aptamers of the present disclosure can directly bind to a cell surface having an affinity on *Klebsiella pneumoniae* without breaking down the cells, thus enabling a prompt and accurate detection of the presence and concentration of *Klebsiella pneumoniae*.

The aptamer may include nucleotide sequences of SEQ. ID. NO: 1-SEQ. ID. NO: 25 or combinations thereof, for example, a nucleotide sequence of SEQ. ID. NO: 2. The above aptamer may include a nucleotide sequence which has 90% or higher homology with any of SEQ. ID. NO: 1-SEQ. ID. NO: 25, for example, any of nucleotide sequences of SEQ. ID. NO: 1-SEQ. ID. NO: 25, where any nucleotide underwent a substitution, an insertion, a deletion, an addition, or combinations thereof.

The aptamer may include a detectable label attached thereto. The detectable label may be a moiety which can be detected by a known detection method in the art, for example, an optical label, an electrochemical label, a radioisotope or combinations thereof. The label may bind to a particular structure, for example, a particular domain of a hairpin-loop structure, or a 3' terminus or 5'-terminus of the aptamer.

The optical label may be, for example, a fluorescent material. The fluorescent material may be selected from the group consisting of fluorescein, 6-FAM, rhodamine, Texas Red, tetramethylrhodamine, carboxyrhodamine, carboxyrhodamine 6G, carboxy rhodol, carboxy rhodamine 110, Cascade Blue, Cascade Yellow, Coumarin, Cy2 (cyanine 2), Cy3, Cy3.5, Cy5, Cy5.5, Cy-chrome, phycoerythrin, peridinin chlorophyll-a protein (PerCP), PerCP-Cy5.5, JOE(6-carboxy-4',5'-dichloro-2',7'-dimethoxyfluorescein), NED, ROX (5-(and 6)-carboxy-X-rhodamine), HEX, Lucifer Yellow, Marina Blue, Oregon Green 488, Oregon Green 500, Oregon Green 514, Alexa Fluor, 7-amino-4-methylcoumarin-3-acetic acid, BODIPY FL, BODIPY FL-Br 2, BODIPY 530/550, conjugates thereof, and mixtures thereof. For example, the fluorescent material may be fluorescein, Cy3 or Cy5.

Additionally, the optical label may be an enzyme. The enzyme may be one used in an enzyme-linked immunosorbent assay (ELISA). The enzyme used in an ELISA may be alkaline phosphatase, horseradish peroxidase, luciferase, or glucose oxidase. When an enzyme is used as the optical label, in order to induce a chemiluminescence reaction, luminol, isoluminol, luciferin, lucigenin, 3-(2'-Spiroadamantane)-4-methoxy-4-(3"-phosphoryloxy)phenyl-1,2-dioxetane (AMPPD), and disodium 3-(4-methoxyspiro{1,2-dioxetane-3,2'-(5'-chloro)tricyclo[3.3.1.13,7]decan}-4-yl)phenyl phosphate (CSPD) may be used as a chemiluminescent material. Furthermore, other chemiluminescent materials may be also used as appropriately selected by one of ordinary skill in the art.

The optical label may be a fluorescence resonance energy transfer (FRET) pair which includes a donor chromophore and an acceptor chromophore separated from each other by a suitable distance, and the emission of fluorescent light by the donor is inhibited by the acceptor. The donor chromophore may include FAM, TAMRA, VIC, JOE, Cy3, Cy5 and Texas Red. The acceptor chromophore may be selected so that its excitation spectrum may be overlapped with the emission spectrum of the donor chromophore. Additionally, the acceptor chromophore may be a non-fluorescent acceptor which quenches a broad spectrum of donors. Other examples of donor-acceptor FRET pairs are already known in the art.

The electrochemical label includes an electrochemical label known in the art, for example, methylene blue.

In another aspect of the present disclosure, there is provided a composition for detecting *Klebsiella pneumoniae*, the composition including a single-stranded nucleic acid aptamer which specifically binds to *Klebsiella pneumoniae*.

In the composition, the aptamer may be one which specifically binds to *Klebsiella pneumoniae*, in particular, one which specifically binds to the cell surface of *Klebsiella pneumoniae*. The aptamer may include nucleotide sequences of SEQ. ID. NO: 1 to SEQ. ID. NO: 25 or combinations thereof, for example, nucleotide sequences of SEQ. ID. NO: 2. The nucleic acid may include DNA RNA, peptide nucleic acid (PNA) or any combinations thereof, for example, DNA. The aptamer may include a detectable label attached thereto, for example, an optical label, a radioisotope or combinations thereof.

The composition may further include a material known to be required for forming a *Klebsiella pneumoniae*-aptamer complex. The composition may further include a factor required for promoting the formation of a specific *Klebsiella pneumoniae*-aptamer complex or for inhibiting the formation of a non-specific *Klebsiella pneumoniae*-aptamer complex, for example, salmon sperm DNA, BSA, Tween-20, and/or PEG.

In a further aspect of the present disclosure, there is provided a sensor for detecting *Klebsiella pneumoniae* including a single-stranded nucleic acid aptamer which specifically binds to *Klebsiella pneumoniae*.

In the sensor, the aptamer may be one which specifically binds to *Klebsiella pneumoniae*, in particular, one which specifically binds to the cell surface of *Klebsiella pneumoniae*. The aptamer may include nucleotide sequences of SEQ. ID. NO: 1 to SEQ. ID. NO: 25 or combinations thereof, for example, nucleotide sequences of SEQ. ID. NO: 2. The nucleic acid may include DNA RNA, peptide nucleic acid (PNA) or any combinations thereof, for example DNA. The aptamer may include a detectable label attached thereto, for example, an optical label, an electrochemical label or combinations thereof. The sensor including the optical label may be, for example, a sensor which utilizes an FRET effect or an enzyme reaction. The sensor including the electrochemical label may be, for example, based on the principle that an electrochemical signal changes as target material moves away from an electrode or moves toward an electrode separated from the aptamer due to a structural change in the aptamer.

The sensor may be one which includes a substrate where the aptamer is immobilized, for example, be an array form. The array herein refers to a state where a plurality of particular molecules are immobilized and fixed to a certain region on the substrate. The array may include an immobilization region formed on the substrate and which includes an aptamer capable of binding to *Klebsiella pneumoniae*. The aptamer may be covalently attached to the substrate within the immobilization region. The aptamer may further include a plurality of compounds with functional groups that may be covalently attached to the substrate. The functional groups may be anything as long as it is capable of attaching the aptamer to the substrate, for example, an aldehyde, an epoxy, or an amine group. Each of the compounds may be a siloxane having an aldehyde, an epoxy, or an amine group at its ends. The material for the substrate may be, for example, glass, silicone, polypropylene, and polyethylene.

In still another aspect of the present disclosure, there is provided a kit for detecting *Klebsiella pneumoniae* including a single-stranded nucleic acid aptamer which specifically binds to *Klebsiella pneumoniae*.

In the kit, the aptamer may be one which specifically binds to *Klebsiella pneumoniae*, in particular, one which specifically binds to the cell surface of *Klebsiella pneumoniae*. The aptamer may include nucleotide sequences of SEQ. ID. NO: 1-SEQ. ID. NO: 25 or combinations thereof, for example, nucleotide sequences of SEQ. ID. NO: 2.

The nucleic acid of the aptamer may be DNA, RNA, PNA or combinations thereof, for example, DNA. The aptamer may have a detectable label attached thereto. The detectable label may be, for example, an optical label, an electrochemical label or combinations thereof.

The kit may be in the form of a chip where the aptamer is immobilized on the chip, or in the form of an array where the aptamer is immobilized on the substrate. The immobilization of DNA aptamers on a chip or a substrate may be performed by using a known method in the art. For example, a chip or a substrate may be modified with streptavidin, an end of an aptamer is biotinylated and then the biotin of the aptamer and the streptavidin of a support are bonded together to be immobilized. The array may include an immobilization region which includes a substrate and an aptamer formed on the substrate and capable of binding to *Klebsiella pneumoniae*. The aptamer may be one covalently attached to the immobilization region. The aptamer may further include a plurality of compounds with functional groups that may be covalently attached to the substrate or the chip. The functional group may be anything as long as it is capable of attaching the aptamer to the substrate or the chip, for example, aldehyde, epoxy, or amine group. The compound may be may be siloxane with aldehyde, epoxy or amine group at the end. The material for the substrate may be, for example, glass, silicone, polypropylene, polyethylene, etc. Additionally, the kit may further include a manual regarding a method for confirming the presence of Klebsiella pneumoniae in a sample by using the aptamer.

In another aspect, there is provided a method for detecting Klebsiella pneumoniae. The method for detecting Klebsiella pneumoniae may include: contacting a sample with the single-stranded nucleic acid aptamer which includes DNA, RNA, PNA or combinations thereof and binds specifically to Klebsiella pneumoniae; measuring a signal from a Klebsiella pneumoniae-aptamer complex formed by the contact; and confirming a presence or concentration of Klebsiella pneumoniae in the sample.

In an exemplary embodiment of the present invention, Klebsiella pneumoniae may be detected by using a method shown below. First, a sample is contacted with a single stranded nucleic acid aptamer which specifically binds to Klebsiella pneumoniae. The contact may be performed in a reaction solvent. For example, the contact may be performed in a reaction solvent which includes a base composition where the aptamer can bind well to Klebsiella pneumoniae, and a factor which prevents a non-specific binding. The factor which prevents a non-specific binding may include, for example, salmon sperm DNA, BSA and/or Tween-20, PEG. The reaction temperature may be, for example, between about 15° C. to about 25° C., between about 20° C. to about 30° C., or between about 20° C. to about 25° C. The reaction time may be between about 20 minutes to about 60 minutes, between about 30 minutes to about 50 minutes, or between about 40 minutes to about 50 minutes. The aptamer may be one which specifically binds to the cell surface of Klebsiella pneumoniae. The aptamer may have a nucleotide sequence including SEQ. ID. NO: 1 to 25 or combinations thereof, for example, a nucleotide sequence including SEQ. ID. NO: 2. The aptamer may have a detectable label attached thereto. The detectable label may be, for example, an optical label, an electrochemical label, a radioisotope or combinations thereof.

Then, the method for detecting Klebsiella pneumoniae may include measuring a signal from a Klebsiella pneumoniae-aptamer complex formed by the contact. The signal from the Klebsiella pneumoniae-aptamer complex may be generated by an optical label (e.g. fluorescence, enzyme), an electrochemical label or combinations thereof. The optical label may be, for example, a donor-acceptor FRET pair. The optical label may be horseradish peroxidase. The electrochemical label may be, for example, methylene blue.

Additionally, the method for detecting Klebsiella pneumoniae may include confirming the presence or concentration of Klebsiella pneumoniae in a sample. The confirmation of the presence or concentration of Klebsiella pneumoniae in a sample may be performed by comparing the presence or concentration in the sample to that in a control group. The control group may be aptamers which are in a state not bound to Klebsiella pneumoniae. For example, when the label attached to the aptamer is a donor-acceptor FRET pair, the control group may be an aptamer where the fluorescent signal of a donor chromophore is inhibited by the acceptor chromophore. A Klebsiella pneumoniae-aptamer complex, once it formed, reduces the FRET efficiency and thereby changes the fluorescent signal, and the presence or concentration of Klebsiella pneumoniae can be confirmed based on the fluorescent signal. For example, when the label attached to the aptamer is an enzyme, the control group may be an enzyme attached to an aptamer which cannot recognize Klebsiella pneumoniae. A Klebsiella pneumoniae-aptamer complex, when formed, changes the color signal of the enzyme according to change in the enzyme reactivity to substrate, whereas the color signal does not change if a Klebsiella pneumoniae-aptamer complex is not formed, and the presence or concentration of Klebsiella pneumoniae can be confirmed based on whether the color signal changes. For example, when the label attached to the aptamer is an electrochemical label, the control group may be the labeled aptamer, which is immobilized to an electrode. When the electrochemical label moves away from or moves toward the electrode or is separated from the aptamer due to the structural change in the aptamer bound to Klebsiella pneumoniae, a change in the electrochemical signal results, and the presence or concentration of Klebsiella pneumoniae can be confirmed based on the change in the electrochemical signal.

The method may further include separating the Klebsiella pneumoniae-aptamer complex from a reactant including the sample and the aptamer. The separation may be performed after formation of the Klebsiella pneumoniae-aptamer complex and before measuring the signal of the Klebsiella pneumoniae-aptamer complex. The separation may be performed, for example, by a membrane filtration method or centrifugation. Additionally, when the aptamer is immobilized on a substrate, the separation may be performed by washing. The optical label attached to the aptamer may be a fluorescent material as described above, for example, fluorescein, Cy3 or Cy5. The signal generated from the separated Klebsiella pneumoniae-aptamer complex may be measured, for example, by fluorimetry or a radioisotope detection method.

In an exemplary embodiment of the present disclosure, the presence and concentration of Klebsiella pneumoniae can be accurately detected and measured by using a simple stranded nucleic acid aptamer which specifically binds to Klebsiella pneumoniae.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
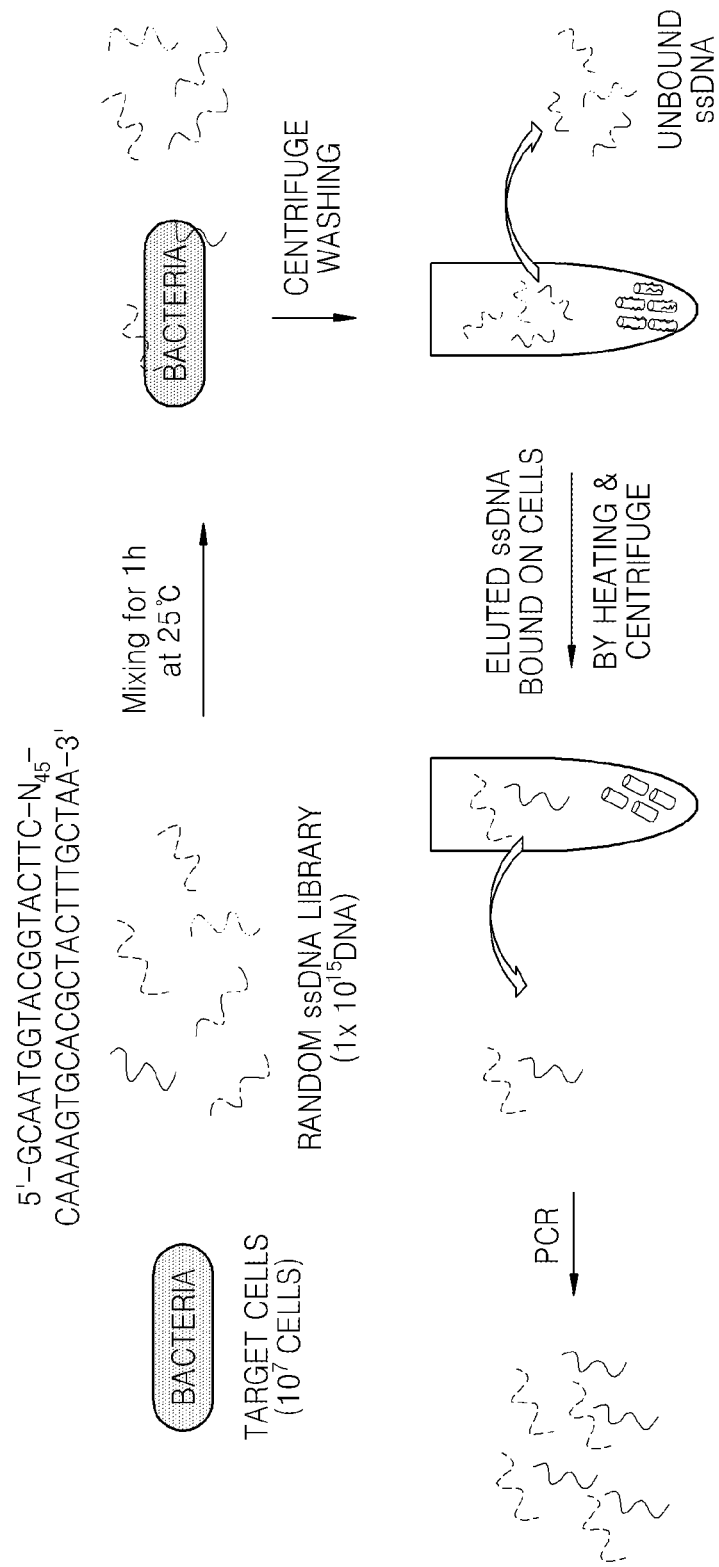
FIG. 1 is a diagram illustrating Bacteria Cell-Systematic Evolution of Ligands by EXponential enrichment (SELEX) method for selecting DNA aptamers which are capable of selectively binding to Klebsiella pneumoniae.
Figure 2:
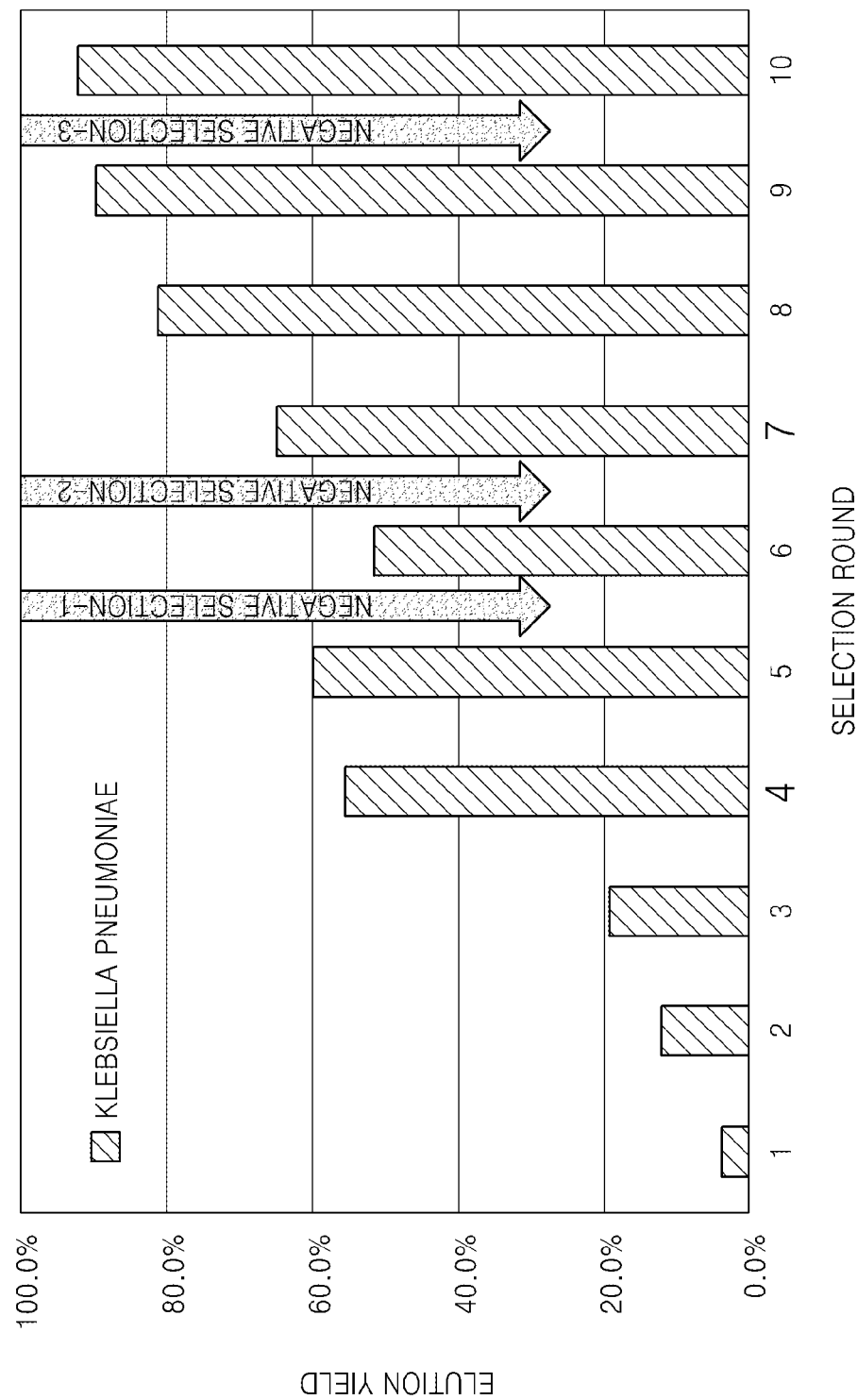
FIG. 2 is a graph illustrating a percentage (%) of ssDNA in the ssDNA library used in each selection round which binds Klebsiella pneumoniae.
Figure 3:
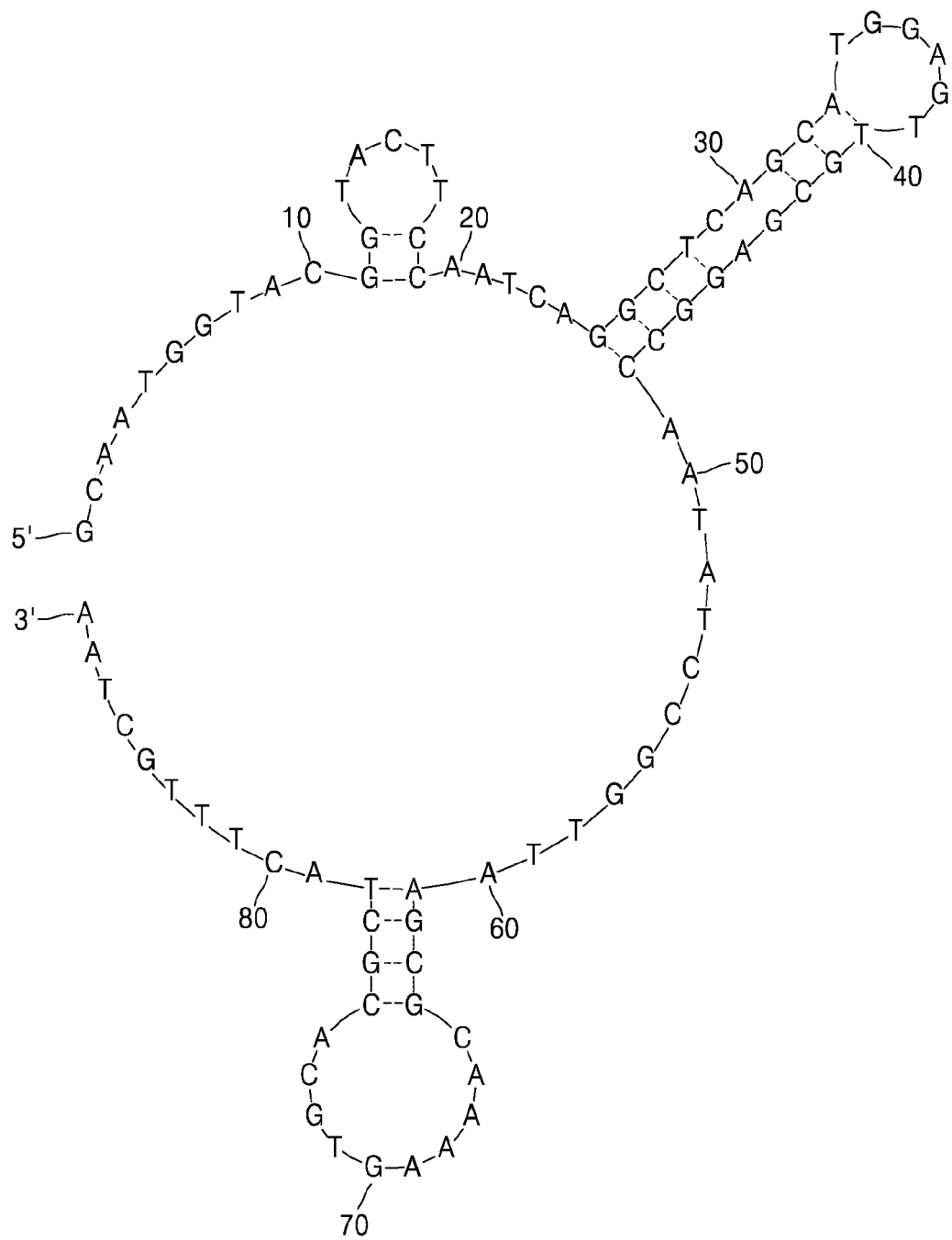
FIG. 3 is a diagram illustrating a secondary structure of a type of DNA aptamer (K2) (SEQ ID NO: 2) [together with forward primer (SEQ ID NO: 27) and reverse primer (SEQ ID NO: 28); c.f., SEQ ID NO: 26] selectively binding to Klebsiella pneumoniae predicted by using an mfold program.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items.

EXAMPLES

Example 1

Preparation of a DNA Aptamer Specifically Binding to *Klebsiella pneumoniae*

1.1 Cultivation of *Klebsiella pneumoniae*

Feces-derived *Klebsiella pneumoniae* sp. (KCTC2208) was inoculated in a nutrient broth (37% beef extract, 63% pepton, and 8 g broth/L of distilled water, at pH 6.8) and cultured at 37° C. until the concentration of the *Klebsiella pneumoniae* sp. (KCTC2208) reached $10^8$ colony forming unit (CFU)/mL. Then, the resultant was washed 3 times with PBS to remove the culture liquid, and suspended in a binding buffer (1×PBS, 0.1 mg/mL salmon sperm DNA, 1% BSA, and 0.05% tween-20).

1.2 Synthesis of an Single-Stranded DNA (ssDNA) Library

In order to selectively screen *Klebsiella pneumoniae*, a ssDNA library consisting of the following ssDNA oligonucleotides was synthesized. The ssDNA library was consist of random ssDNA oligonucleotides respectively with a total length of 88-mer, where the ssDNA oligonucleotide has a fixed nucleotide sequence region (underlined) to which a primer pair is annealed at both ends, and a randomly arrayed nucleotide sequence region ($N_{45}$) in the center. In particular, $N_{45}$ generally refers to a constitution consisting of 45 random bases of A, G, T and C. However, the total number of bases is not limited to 45, as a few bases may be added or omitted via repeated PCR and cloning of SELEX process, and the length of the 88-mer of the finally synthesized ssDNA may be also changed.

(SEQ. ID. NO: 26)
5'-<u>GCAATGGTACGGTACTTCC</u>-$N_{45}$-

<u>CAAAAGTGCACGCTACTTTGCTAA</u>-3'

Finally, a random ssDNA library having $10^{15}$ mutually different nucleotide sequences was synthesized.

1.3 Whole-Cell SELEX Process

1) Selection and Separation of ssDNA

The synthesized ssDNA library was melted in a binding buffer (1×PBS, 0.1 mg/mL salmon sperm DNA, 1% BSA, and 0.05% tween-20) and heated at 95° C. for 5 minutes, and then immediately cooled at 4° C. for 10 minutes. Then, the resultant was mixed with 1 mL of *Klebsiella pneumoniae* suspension ($10^7$ cells) at room temperature for 1 hour. A *Klebsiella pneumoniae*-ssDNA complex was separated from an ssDNA which was not bound to *Klebsiella pneumoniae* by centrifugation (13,000 rpm, 10 minutes), and the *Klebsiella pneumoniae*-ssDNA complex thus separated from the ssDNA was suspended in PBS. The separation and suspension were each repeated 3 times. Finally, the *Klebsiella pneumoniae*-ssDNA complex was resuspended in sterile distilled water.

In order to separate the ssDNA bound to the surface of *Klebsiella pneumoniae*, the *Klebsiella pneumoniae*-ssDNA complex was heated at 95° C. for 5 minutes, and then immediately cooled at 4° C. for 10 minutes. The ssDNA separated from the surface of *Klebsiella pneumoniae* was recovered by centrifugation (13,000 rpm, 10 minutes).

The ssDNA thus separated from the surface of *Klebsiella pneumoniae* was amplified via a Polymer Chain Reaction (PCR). The two primers used for the PCR are shown below. The 5' terminus of a forward primer was labeled with fluorescein, and the 5' terminus of a reverse primer was labeled with biotin. The different labeling was used to separate the double stranded dsDNA of the PCR products into ssDNA.

forward:
(SEQ. ID. NO: 27)
5'-fluorescein-GCAATGGTACGGTACTTCC-3' reverse:
(SEQ. ID. NO: 28)
5'-biotin-TTAGCAAAGTAGCGTGCACTTTTG-3'

PCR was performed under the conditions of 95 (30 seconds), 56.3 (30 seconds) and 72 (10 seconds), with a total of 25 μL volume obtained by mixing 10 μl of ssDNA (which is approximately 100 ng), 1.25 μL of each primers with 10 μM, and 12.5 μl of PCR master mix, and the number of repeating cycle was 10. The PCR products were confirmed by analysis thereof in a 2% agarose gel via electrophoresis. The PCR product was then purified by using a MinElute PCR Purification kit (QIAGEN).

Subsequently, only the required ssDNA portions in dsDNA with a double helix structure of the PCR product were isolated by using magnetic beads coated with 50 μL of avidin (Dynabeads MyOne™ Streptavidin, Invitrogen). Then, 100 μL of PCR product was mixed with 50 μL of the magnetic beads, allowed to react for 10 minutes at room temperature, and then washed with 1 mL of PBS buffer by using a magnet. 500 μL of 200 mM NaOH was added thereto, and the mixture was allowed to react for 5 minutes in order to denature dsDNA into ssDNA. Biotin-attached ssDNA was removed from the reacting solution using a magnet, and fluorescein-attached ssDNA was collected. The thus the collected ssDNA was purified/concentrated by using a PCR purification kit, and the concentration of the ssDNA was analyzed. The purified/concentrated ssDNA was used for the next round's selection procedure, and a total of 10 selection procedures were made. Finally, it was confirmed that 92.3% of the ssDNA mixed with *Klebsiella pneumoniae* was bound to *Klebsiella pneumoniae*.

3) Counter Selection

In order to increase the affinity of ssDNA, which were selected during a SELEX process, a counter selection was performed a total of 3 times after 5th, 6th and 9th selection procedures, by using 5 different bacteria including *Eschericia coli, Citrobacter freundii, Enterobacter aerogenes, Bacillus subtilis*, and *Staphylococcus epidermidis*, which are commonly discovered in an aqueous system such as a sewage system as is the case with the targeted *Klebsiella pneumoniae*. The methods and conditions of this counter selection was the same as those used in the prior selection procedure. However, in the counter selection process, the ssDNA which were bound to the bacteria were discarded and only those ssDNA which were not bound to the bacteria were collected and amplified to be used for a subsequent selection process.

1.4 Cloning of ssDNA

The finally obtained ssDNA was amplified via PCR by using primer pairs and cloned by using a cloning kit (TOPO TA cloning kit). Plasmids were isolated from each colony, and nucleotide sequences of the ssDNA were analyzed, and as a result, a total of 25 different nucleotide sequences were obtained. Table 1 below shows the selected 25 different nucleotide sequences of the ssDNA selected by the SELEX process.

TABLE 1

| Name | Nucleotide Sequences in Random Regions |
|---|---|
| K1 | 5'-GAGTCGGTGGTGTTCCCAGATGG AAGCCGCAGTAATAGTGCAGCT-3' (SEQ. ID. NO: 1) |
| K2 | 5'-AATCAGGCTCAGCATGGAGTTGC GAGGCCAATATCCGGTTAAGCG-3' (SEQ. ID. NO: 2) |
| K3 | 5'-TGTCCTTCAGACCCCTGATTTGA TTAATATTCTTAAAGTCTTCAG-3' (SEQ. ID. NO: 3) |
| K4 | 5'-CTTTATAACACTGTTACTATCGC CTGTTAGAGGTAATGAGTTCTT-3' (SEQ. ID. NO: 4) |
| K5 | 5'-ATACCGCATGGATGAGGTGTTGT ACTTGGGTGCTGGGGGGGTCTG-3' (SEQ. ID. NO: 5) |
| K6 | 5'-TTTTACAGCTAAACCGGTGTAAT GTCCTTGTTCTTCATACATACA-3' (SEQ. ID. NO: 6) |
| K8 | 5'-TCTTTTAGGGAGTCCCTATTAAG TATTGTAACCTTAGGACTGAAT-3' (SEQ. ID. NO: 7) |
| K9 | 5'-CTTAACTAGTTGCATGGGTCCTG CTCGAGGGATCGTGGGTGATGG-3' (SEQ. ID. NO: 8) |
| K10 | 5'-ATGACTCATTGGTGCTTCGCATT TTACTGCATCTCCTAATATTGG-3' (SEQ. ID. NO: 9) |
| K11 | 5'-TCTTTTAGGGAGTCCCTATTAAG TATTGTAACCTTAGGACTGAAT-3' (SEQ. ID. NO: 10) |
| K13 | 5'-GGGTGCGCGGGTTAATAGATTTT ATAAAAAGTTGTGCCTGTCGTT-3' (SEQ. ID. NO: 11) |
| K14 | 5'-CGGCAGTTGGTTTTTTCTGTTCT GCATAGGATGCTCTTAGTCGGC-3' (SEQ. ID. NO: 12) |
| K17 | 5'-AGTCTTATGGAGCGGTCGACAAC GTCACCGCCCTGTGGTGAGGT-3' (SEQ. ID. NO: 13) |
| K18 | 5'-ATGGCACCCTTGCAAGCGAACCT GGGTTTTTAGTCGTTAGCATTG-3' (SEQ. ID. NO: 14) |
| K19 | 5'-TCATAGAGTGTAACTAACTAGTC GTTGATGCGGTTGGCTTTAGC-3' (SEQ. ID. NO: 15) |
| K20 | 5'-GATATTGACTAAGAGGTGGTTGT CTCCTTTTGCTAAATCTCGCTC-3' (SEQ. ID. NO: 16) |

TABLE 1-continued

| Name | Nucleotide Sequences in Random Regions |
|---|---|
| K21 | 5'-ATGCACCAGGGATGTATATTGTC TGGCTGTCTTCTTTGGACGCGT-3' (SEQ. ID. NO: 17) |
| K22 | 5'-ATGTGCTGGAAGCGCCACAGGAT TATTGGTGACGTGTTTGCGCTT-3' (SEQ. ID. NO: 18) |
| K23 | 5'-GTTGTGTCTATACTCAGCTTCTT GTTACTTTACTGGACATCTATC-3' (SEQ. ID. NO: 19) |
| K24 | 5'-GGGAGCTTATGTAGAAGCAAAGG TGCGATGCTGGGTGAGCGTTA-3' (SEQ. ID. NO: 20) |
| K25 | 5'-TTACGAGCGGGCGGGGTTTAGTG TTTCTGTGGGTTCTGTTTCATA-3' (SEQ. ID. NO: 21) |
| K26 | 5'-GCAACTGGATTACGTACCTTGCT TTGTGAACTTACTTGTCACCCA-3' (SEQ. ID. NO: 22) |
| K27 | 5'-CGACCACACTTCCCTGGAACTCT GAGTTGGCACTCTGCCGCAGCT-3' (SEQ. ID. NO: 23) |
| K28 | 5'-CGGCTTCATTTCTGTGTTGGTTG CGTTTGTGTGGGGATTTCTCAT-3' (SEQ. ID. NO: 24) |
| K29 | 5'-GTTGTGTCTATACTCAGCTTCTT GTTACTTTACTGGACATCTATC-3' (SEQ. ID. NO: 25) |

2.1 Affinity Analysis of Aptamers on *Klebsiella pneumoniae*

In order to analyze the affinity of the aptamers on *Klebsiella pneumoniae*, a nutrient broth ((beef extract 37%, pepton 63%, 8 g broth/L D.W, and pH 6.8) was inoculated with *Klebsiella pneumoniae* (KCTC2208), and cultured at 37° C. until the concentration of *Klebsiella pneumoniae* reached $10^8$ CFU/mL. To remove the nutrient media from the *Klebsiella pneumoniae*, the *Klebsiella pneumoniae* was washed 3 times with PBS buffer and then suspended in a binding buffer (1×PBS, 0.1 mg/mL of salmon sperm DNA, 1% BSA, 0.05% tween-20). 100 μL ($10^7$ cells) of *Klebsiella pneumoniae* was mixed with 100 μL of fluorescence-labeled ssDNA at various concentrations (0, 2.5, 5, 10, 25, 50, 100, 250, 500 nM), and allowed to react at room temperature for 45 minutes. Upon reaction, the resultants were washed twice with PBS buffer to remove the ssDNA which was not bound to the surface of *Klebsiella pneumoniae*, and the fluorescence intensity of the *Klebsiella pneumoniae*-ssDNA complex was measured by using a fluorometer.

Figure 4:
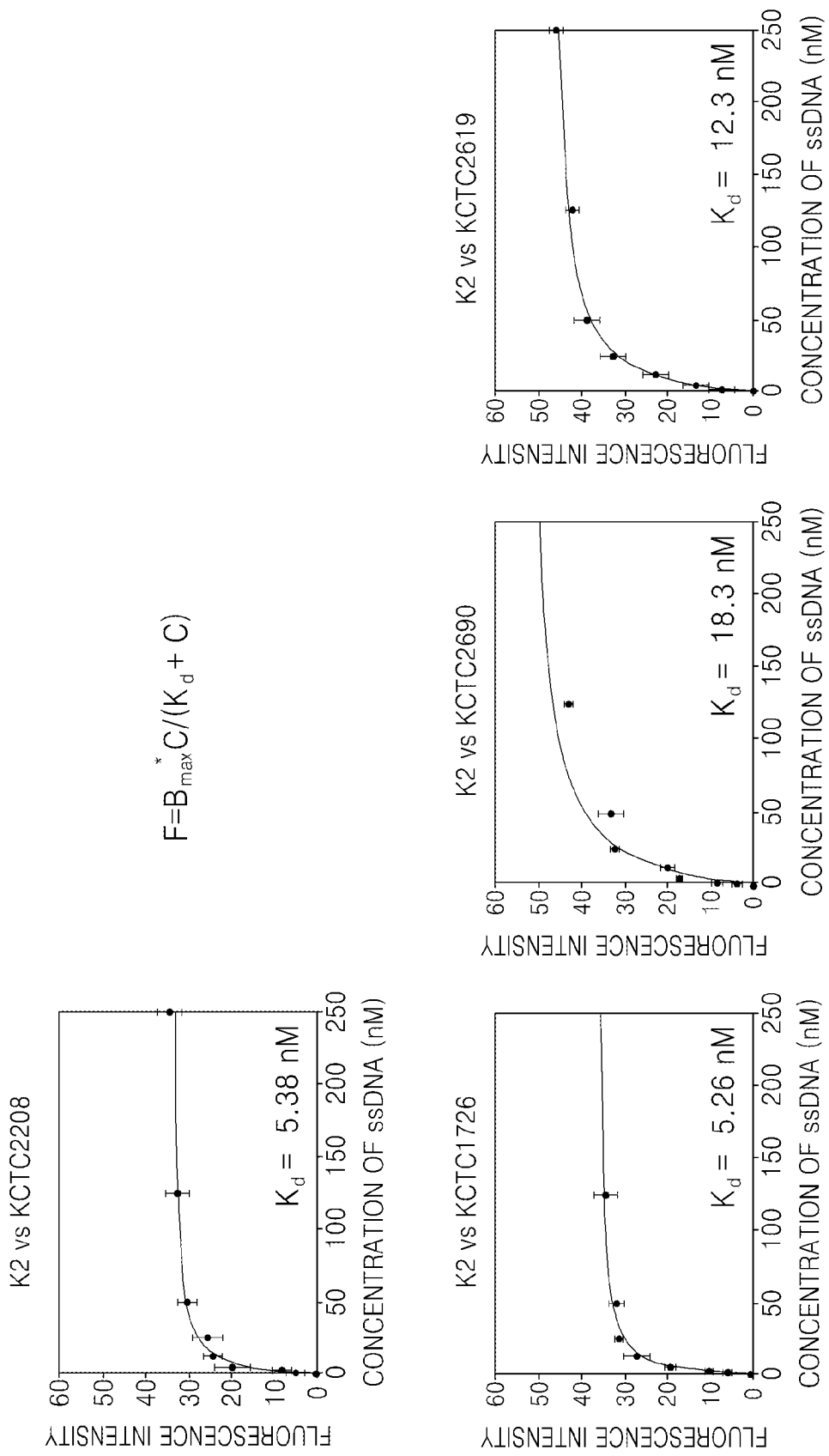
FIG. 4 is a graph illustrating affinity analysis of 4 kinds of Klebsiella pneumoniae with respect to a type of DNA aptamer which selectively binds to Klebsiella pneumoniae.

The fluorescence intensity at each of the various ssDNA concentrations was plotted in a graph via a non-linear regression method and single-region saturation ligand binding method by using a SigmaPlot program based on the equation, $F=B_{max}*C/(K_d+C)$, wherein F indicates the fluorescence intensity, $B_{max}$ indicates the location of maximum binding, $K_d$ indicates a dissociated constant, and C indicates concentration of ssDNA. As a result of the above affinity analysis, a type of ssDNA having the highest affinity for *Klebsiella pneumoniae* is shown in FIG. 4. The binding strength ($K_d$: dissociation constant) of the ssDNA (K2) having the highest affinity for *Klebsiella pneumoniae* is shown in Table 2 below.

TABLE 2

| ssDNA | Dissociation constant ($K_d$) |
|---|---|
| K2 | 5.377 nM |

Binding strength of ssDNA K2 to *Klebsiella pneumoniae* KCTC2208

Additionally, the affinity of the ssDNA (K2) on the three remaining types of *Klebsiella pneumoniae* (KCTC1726, KCTC2619, and KCTC2690) was analyzed. In particular, 100 μL of *Klebsiella pneumoniae* ($10^7$ cells) was allowed to react with 100 μL of 500 nM ssDNA at room temperature for 45 minutes, washed with PBS buffer, and the fluorescence intensity of each of the *Klebsiella pneumoniae*—ssDNA complexes was measured and compared. The fluorescence intensity of the *Klebsiella pneumoniae*—ssDNA complexes was measured by using a fluorometer in the same manner used for measuring the intensity of (*Klebsiella pneumoniae*) KCTC2208. As a result of the affinity analysis, it was confirmed that ssDNA (K2) has the highest affinity for each of the *Klebsiella pneumoniae* strains, and the binding strength ($K_d$: dissociation constant) of ssDNA (K2) to each of the *Klebsiella pneumoniae* species is shown in Table 3 below.

TABLE 3

Binding strength of ssDNA (K2) to each of three *Klebsiella pneumoniae* strains

| *Klebsiella pneumoniae* strain | Dissociation Constant ($K_d$) |
|---|---|
| KCTC1726 | 5.2648 nM |
| KCTC2619 | 12.3043 nM |
| KCTC2690 | 18.3279 nM |

2-2. Affinity Analysis of Aptamers on *Klebsiella pneumoniae*

Figure 5:
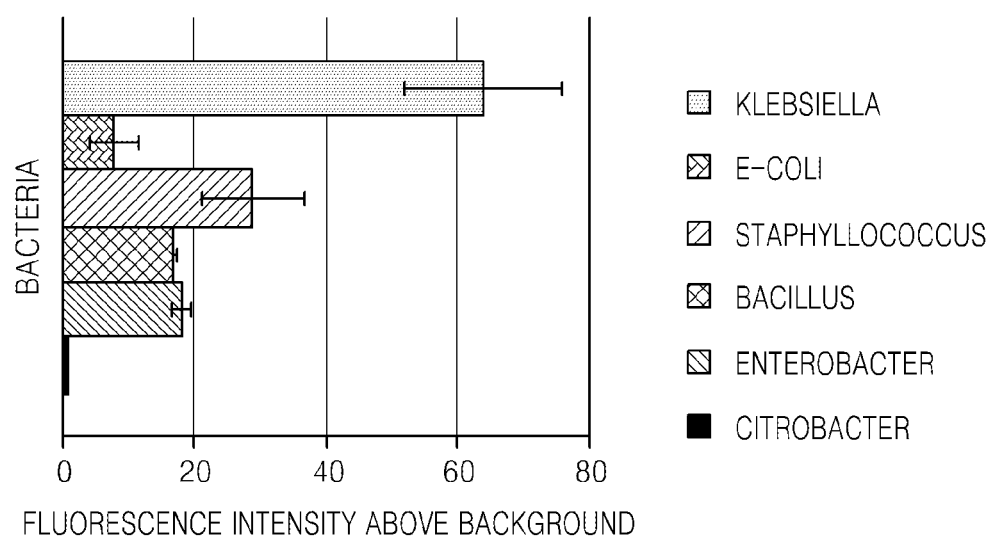
FIG. 5 is a graph illustrating a specificity analysis of a type of DNA aptamer which selectively binds to Klebsiella pneumoniae.

In order to confirm the affinity of the ssDNA (K2) on *Klebsiella pneumoniae*, affinity analysis of the ssDNA (K2) on five other bacteria species, that is, *Escherichia coli, Citrobacter freundii, Enterobacter aerogenes, Bacillus subtilis,* and *Staphylococcus epidermidis*, were performed. 100 μL of each of the five different bacteria species ($10^7$ cells) was allowed to react with 100 μL of 500 nM ssDNA at room temperature for 45 minutes, washed with PBS buffer, and the fluorescence intensity of each of the bacteria—ssDNA complexes was measured and compared. As shown in FIG. 5, the fluorescence intensity of the ssDNA (K2) on the targeted *Klebsiella pneumoniae* was less than 50% of the fluorescence intensity of the ssDNA (K2) when mixed with *Escherichia coli, Citrobacter freundii, Enterobacter aerogenes, Bacillus subtilis,* and *Staphylococcus epidermidis*.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A single-stranded nucleic acid aptamer capable of specifically binding to *Klebsiella pneumoniae*, wherein the aptamer includes any one of nucleotide sequences SEQ ID NO: 1-SEQ ID NO: 25 or combinations thereof.

2. The single-stranded nucleic acid aptamer according to claim 1, wherein the aptamer is capable of binding to the surface of *Klebsiella pneumoniae*.

3. The single-stranded nucleic acid aptamer according to claim 1, wherein the single-stranded nucleic acid comprises DNA, RNA, PNA or combinations thereof.

4. The single-stranded nucleic acid aptamer according to claim 1, wherein the aptamer has a detectable label attached thereto.

5. The single-stranded nucleic acid aptamer according to claim 4, wherein the detectable label is an optical label, an electrochemical label, a radioisotope or combinations thereof.

6. A composition for detecting *Klebsiella pneumoniae* including the single-stranded nucleic acid aptamer according to claim 1.

7. A sensor for detecting *Klebsiella pneumoniae* including the single-stranded nucleic acid aptamer according to claim 1.

8. The sensor for detecting *Klebsiella pneumoniae* according to claim 7, wherein the aptamer is immobilized on a substrate.

9. A method for detecting *Klebsiella pneumoniae*, the method comprising:
- contacting a sample with the single-stranded nucleic acid aptamer according to claim 1;
- measuring a signal from a *Klebsiella pneumoniae*-aptamer complex formed by the contact; and
- confirming a presence or concentration of *Klebsiella pneumoniae* in the sample.

10. The method for detecting *Klebsiella pneumoniae* according to claim 9, further comprising separating the *Klebsiella pneumoniae*-aptamer complex from a reactant including the sample and the aptamer.

* * * * *